United States Patent [19]
Frazier

[11] Patent Number: 5,968,045
[45] Date of Patent: *Oct. 19, 1999

[54] INTRA-ARTICULAR TENDON SLING FIXATION SCREW

[76] Inventor: John K. Frazier, 3191 Stanwood La., Lafayette, Calif. 94549

[ * ] Notice: This patent issued on a continued prosecution application filed under 37 CFR 1.53(d), and is subject to the twenty year patent term provisions of 35 U.S.C. 154(a)(2).

[21] Appl. No.: 08/949,368

[22] Filed: Oct. 14, 1997

[51] Int. Cl.[6] .................................................... A61B 17/86
[52] U.S. Cl. ............................................. 606/73; 606/232
[58] Field of Search .................................. 606/73, 72, 60, 606/77, 86, 88, 104, 232; 623/13

[56] References Cited

U.S. PATENT DOCUMENTS

| | | |
|---|---|---|
| D. 331,463 | 12/1992 | Rosenberg et al. . |
| 4,632,100 | 12/1986 | Somers et al. . |
| 4,870,957 | 10/1989 | Goble et al. . |
| 4,950,270 | 8/1990 | Bowman et al. . |
| 5,102,421 | 4/1992 | Anspach, Jr. et al. . |
| 5,129,902 | 7/1992 | Goble et al. . |
| 5,152,790 | 10/1992 | Rosenberg et al. . |
| 5,156,616 | 10/1992 | Meadows et al. . |
| 5,370,662 | 12/1994 | Stone et al. . |
| 5,374,269 | 12/1994 | Rosenberg . |
| 5,443,482 | 8/1995 | Stone et al. . |
| 5,470,334 | 11/1995 | Ross et al. ................................. 606/72 |
| 5,534,011 | 7/1996 | Greene, Jr. et al. ..................... 606/232 |
| 5,674,224 | 10/1997 | Howell . |

OTHER PUBLICATIONS

Stephen M. Howell, MD, Arthrotek Brochure "Tunneloc Bone Mulch Screw Technique", date unknown.

*Primary Examiner*—Michael Buiz
*Assistant Examiner*—David O. Reip
*Attorney, Agent, or Firm*—Charles R. Cypher; James R. Cypher

[57] ABSTRACT

The present invention teaches a fixation screw for securing a graft to a bone. The fixation screw is formed with a body member having a distal end, a proximal end, a central axis, and a cannula through the central axis of the body member. The body member also has a shank portion which is formed with an external screw thread, and a head portion rigidly coupled to the shank portion. The head portion is formed to mechanically couple with a driver and also to directly receive the graft which the fixation screw anchors.

1 Claim, 9 Drawing Sheets

INTRA-ARTICULAR TENDON SLING FIXATION SCREW

BACKGROUND OF THE INVENTION

This invention relates to an anchoring device for use in reconstructing torn ligament connections, such as the anterior cruciate ligament (ACL) in the knee. Specifically, this invention relates to an improved fixation screw, called an intra-articular tendon sling fixation screw by the inventor, which is formed as a unitary construct. The fixation screw has a threaded shank portion that can be inserted into bone and a head portion formed with an eyelet through which a graft, such as an autograft, an allograft or a prosthetic ligament, can be looped.

The fixation screw of the present invention is particularly suited for reconstructive surgery in which the fixation screw is preferably inserted completely into bone and directly receives the graft. As such, the present invention is particularly suited for ACL reconstruction and for posterior cruciate ligament (PCL) reconstruction in the knee. It is to be noted that ACL reconstruction has become a common operation. On the other hand, PCL reconstruction surgery is performed much less often as significant knee function can be maintained without the benefit of the PCL. Thus, for illustrative purposes, this specification will focus on ACL reconstruction surgery to illustrate the use, function and benefits of the present invention.

Reconstructive surgeries of the ACL date back as far as 1904. Since that time, a variety of different methods and devices for aiding in the reconstruction of the ACL have been patented and described. Most modern techniques utilize arthroscopic procedures to minimize the size of any incisions made. U.S. Pat. No. 5,374,269, granted to Thomas D. Rosenberg on Dec. 20, 1994 (hereinafter referred to as Rosenberg '269) is illustrative of the prior art. Rosenberg '269 describes variations on a number of common techniques of ACL reconstruction.

Rosenberg '269 specifically claims a method of forming a passageway in a femur at the knee joint. Its specification does not limit itself, however, to only describing this specific sub-procedure. Rosenberg '269 describes two ACL reconstruction methods that use the patellar tendon as the graft and one method that uses the semitendinosus tendon. Both the patellar tendon and the semitendinosus tendon can be harvested from the individual having the knee surgery and are, therefore, autografts. These tendons are commonly used as the replacement graft for the torn or ruptured ACL. In each of the methods described in Rosenberg '269, tunnels are drilled in the tibia and the femur. These tunnels end in the intra-articular space of the joint at the attachment sites of the torn or ruptured ACL. The tunnel in the tibia goes from the tibial cortex at a site between 20 and 25 mm below the knee joint to the intra-articular space of the knee joint. The tunnel in the femur is a closed-end tunnel, although it may be formed with a channel that extends to the lateral surface of the femur, depending on the graft attachment method used. Rosenberg '269 modifies the prior art method of drilling the femoral tunnel, but is otherwise indicative of an accepted practice for forming the femoral and tibial tunnels.

In Rosenberg '269, the graft, whether a patellar tendon or a semitendinosus tendon, is implanted with one end secured in the closed-end femoral tunnel and the other end secured in the tibial tunnel or at a point adjacent to the tibial tunnel on the tibial cortex.

In the first method described by Rosenberg '269, using the patellar tendon, the bone plug on the leading end of the graft can be locked in place in the femoral tunnel with an interference screw. Rosenberg '269 also teaches a method by which the leading end bone plug is attached with sutures that are anchored to the lateral femoral cortex by means of a button. The sutures pass through a channel that extends from the closed end of the femoral tunnel to the lateral surface of the femur. The sutures attach to the leading bone plug. In both methods using the patellar tendon, the trailing bone plug is secured by staples to the tibial cortex below the tibial tunnel entrance.

Rosenberg '269 also describes a method for anchoring the semitendinosus tendon. Elongated sutures are attached to the ends of the semitendinosus tendon graft. The leading end of the graft is secured in a manner similar to the second method for securing the patellar tendon in the femoral tunnel described above. That is by means of sutures attached to a button on the lateral femur cortex, which are passed through a channel to the end of the femoral tunnel where they attach to the semitendinosus graft. The trailing edge of the graft is secured in the tibial tunnel by means of sutures that are affixed to a screw or post positioned on the tibia adjacent to the entrance of the tibial tunnel.

While the methods of preparing tunnels in the bones of the knee joint taught by Rosenberg '269 are applicable to methods using the present invention, the present device differs materially from any device taught in Rosenberg '269. The fixation screw of the present invention is an anchor. Rosenberg '269 teaches an interference screw. Furthermore, use of the fixation screw of the present invention requires vastly differing attachment methods for grafts than the methods taught by Rosenberg '269. First, the inventor prefers not to use the patellar tendon as a graft for ACL reconstruction. Second, when the fixation screw of the present invention is used with the semitendinosus tendon, there is no need to form a channel from the closed-end tunnel in the femur to the surface of the femoral cortex, nor is there a need to make a lateral incision at the lateral femoral cortex as is necessary with the method described by Rosenberg '269. Thus, methods employing the present invention reduce the number of incisions made and trauma to the femur or other bone in which the fixation screw is inserted. They also do not require the use of sutures for anchoring the leading end of the semitendinosus tendon in the femoral tunnel.

While the present invention differs from the devices and methods taught by Rosenberg '269 in both form and use, two endosteal ligament retaining devices have been described that are more similar to the present invention in the methods by which they anchor a graft in the femur. They are U.S. Pat. No. 5,129,902, entitled "Endosteal Ligament Retainer," granted to E. Marlowe Goble and Karl Somers on Jul. 14, 1992 (hereinafter referred to as Goble '902) and U.S. Pat. No. 5,152,790, entitled "Ligament Reconstruction Graft Anchor Apparatus," granted to Thomas D. Rosenberg, Gerard S. Carlozzi and William J. Reimels on Oct. 6, 1992 (hereinafter referred to as Rosenberg '790). Like the present invention, these inventions teach an anchor inserted into a closed-end femoral tunnel that receives a graft. Also like the present invention, both of these devices are used in methods where the closed-end femoral tunnel is formed in the femur in a fashion similar to Rosenberg '269. However, like the method for which the present invention is designed and unlike Rosenberg '269, these methods and devices do not need a channel formed in the femur that passes from the closed-end tunnel to the lateral femoral cortex.

Goble '902 teaches an anchor consisting of a basket or disk for receiving a graft which is rotatably attached to a screw. The graft receiving disk or basket is able to spin on the screw head, preventing the graft from twisting or rotating as the screw is driven into the closed end of the femoral tunnel. The graft can either be looped through an opening in the basket or sutured to the basket.

Rosenberg '790 also teaches an anchor assembly consisting of a basket, called a ring in this case, for receiving the graft which is rotatably attached to a threaded body member. Like Goble '902, the graft receiving basket is able to spin on the threaded body member. Rosenberg '790, however, teaches suturing the graft to the ring.

There are a number of material differences between the prior art and the present invention. Both Goble '902 and Rosenberg '790 are multi-component anchors having moving parts. This can lead to complications. Furthermore, because the diameter of the basket of Goble '902 is much larger than the threads of the fixation screw, it could become wedged against the edge or side of the femoral tunnel during installation, making it difficult to fully insert or retrieve the anchor. It is to be noted that both Goble '902 and Rosenberg '790 teach using sutures as an intermediate means for attaching the graft to the anchor. The sutures are the weak link in the attachment and suture breakage is a consideration. Also, neither of the prior art devices are cannulated for use with a guide drill. Finally, in both Goble '902 and Rosenberg '790, because the means for attachment of the graft are located away from the central axis of the anchor or threaded member, the graft cannot be aligned with the axis of the anchor member, either during or after installation.

Furthermore, in Goble '902, when sutures are not used to attach the graft to the basket, the graft can end up being pinched between the basket and the wall of the femoral tunnel. This is because the graft or grafts must loop through openings in the arcuate walls of the basket on its periphery.

To summarize, the present invention provides a fixation screw that has no moving parts, that can be installed in a closed-end femoral tunnel with the use of a guide drill, receive a graft without the necessity of sutures, receive a graft without causing pinching of the graft between the fixation screw and the wall of the femoral tunnel, and that allows the anchored graft to be aligned with the central axis of the fixation screw.

SUMMARY OF THE INVENTION

It is an object of the present invention to provide a fixation screw for attaching a graft to bone that is of unitary construction.

It is another object of the present invention to provide a fixation screw that can be used with a guide drill.

It is a further object to provide a fixation screw that is self-tapping in bone.

It is a further object of the present invention to provide a fixation screw that can receive a graft ligament without requiring the use of sutures or other additional connective members.

Another object of the present invention is to provide a fixation screw that can directly receive a graft ligament without pinching the graft between the wall of the tunnel and the head portion of the fixation screw.

A further object of the present invention is to provide a fixation screw that can receive a graft that is aligned with the central axis of the fixation screw.

Another object of the present invention is to provide a method of attaching the graft to the fixation screw that allows the graft to be doubled-over, forming a sling thereby increasing the tensile strength of the graft.

Another object of the present invention is to provide a fixation screw that is suitable for anchoring a graft in the femur for reconstructing the anterior cruciate ligament (ACL) of the knee.

A further object of the present invention is to provide a fixation screw that is suitable for arthroscopic ACL reconstruction procedures.

Another object of the present invention is to provide a fixation screw that is suitable to ACL reconstruction procedures that are minimally invasive so as to lessen trauma and facilitate patient rehabilitation.

Another object of the present invention is to provide a fixation screw that is particularly suited for use with either the semitendinosus tendon or the gracilis tendons, or both as the graft to be anchored in ACL reconstruction.

DESCRIPTION OF THE PREFERRED EMBODIMENT OF THE INVENTION

Figure 4:
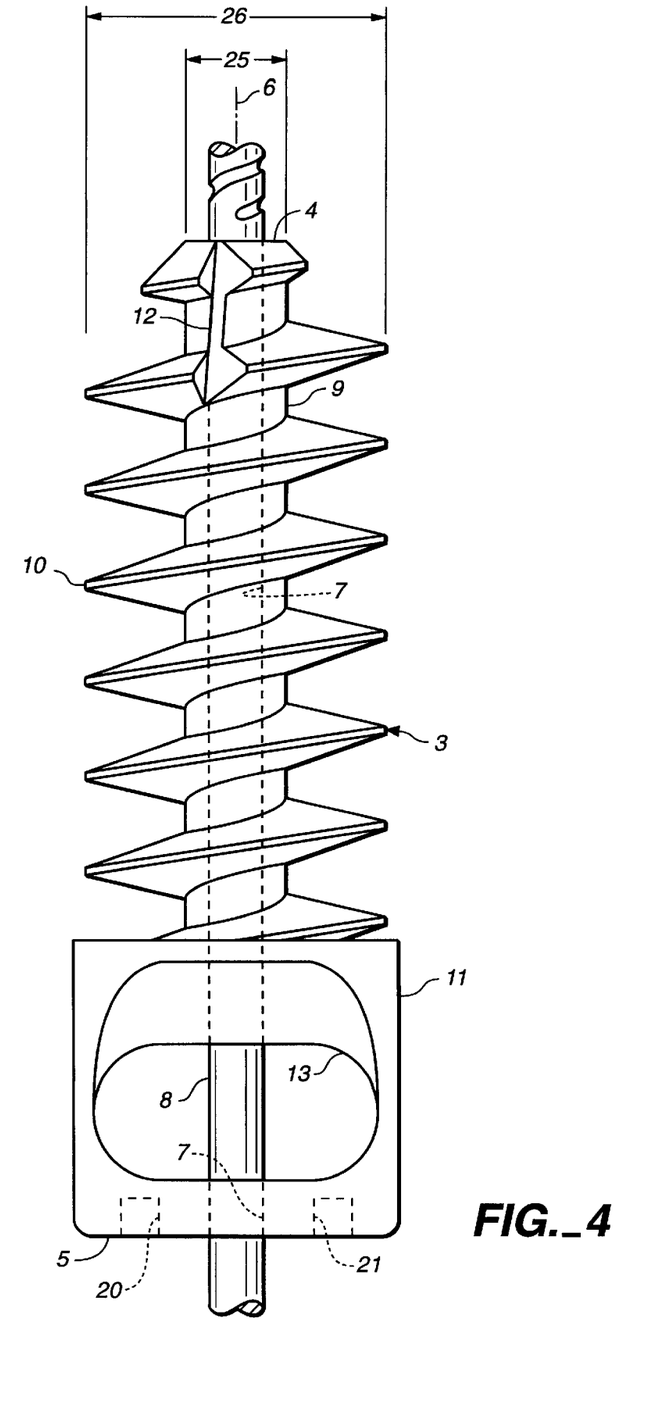
FIG. 4 is a front view of the preferred form of the fixation screw of the present invention inserted over a guide drill. The fixation screw is shown with a cutting flute at its distal end. It is also shown with openings in the proximal end of the body member and head portion that receive corresponding extensions on a matching driver.
Figure 5:
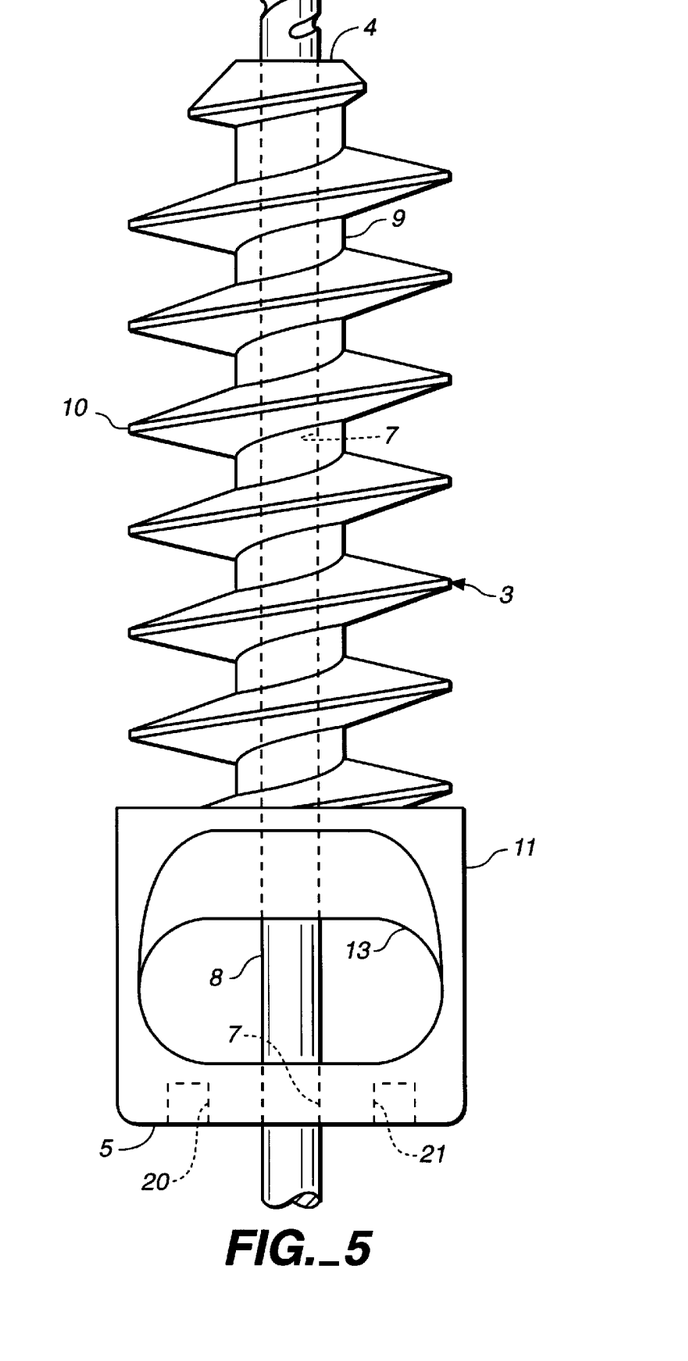
FIG. 5 is a front view of the fixation screw of the present invention inserted over a guide drill. The fixation screw is shown with openings in the proximal end of the body member and head portion that receive corresponding extensions on a matching driver.
Figure 6:
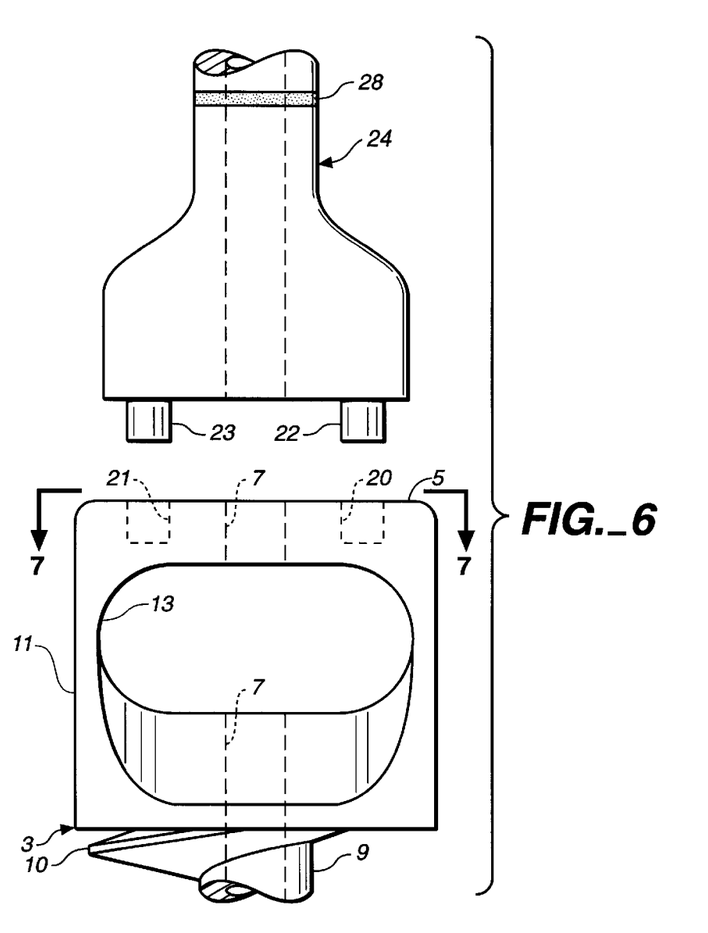
FIG. 6 is a front view of a portion of the fixation screw of the present invention and a portion of a driver for inserting the fixation screw. The head portion and part of the shank portion of the fixation screw are shown. The fixation screw is shown with openings in the proximal end of the body member and head portion that receive corresponding extensions on the driver.
Figure 7:
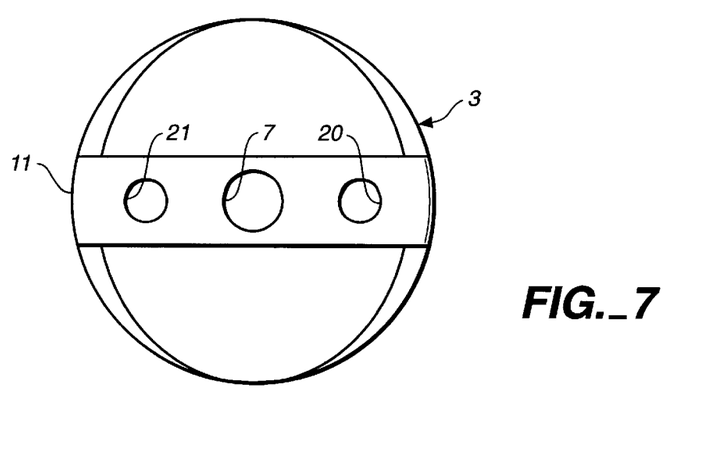
FIG. 7 is a top view of fixation screw of the present invention, showing the head portion of body member, taken generally along line 7—7 of FIG. 6.

The present invention teaches a graft fixation screw for securing a graft 1 to a bone 2. As shown in FIG. 4, the body member 3 of the present invention has a distal end 4, a proximal end 5, a central axis 6 and a cannula 7 through said central axis 6 of said body member 3. The fixation screw is formed with a cannula 7 to allow the fixation screw to be used with a guide drill 8 for ensuring anatomic placement of the fixation screw.

The body member 3 of the fixation screw of the present invention also has a shank portion 9 which is formed with an external screw thread 10, and a head portion 11 rigidly coupled to the shank portion 9. The head portion 11 is formed with means for mechanically coupling with a driver and also with means for securing the graft 1 to the head portion 11.

As is also shown in FIG. 4, in the preferred embodiment of the present invention, the cannula 7 in the shank portion 9 of the body member 3 is dimensioned to closely receive a guide drill 8.

In the preferred embodiment of the present invention, the thread 10 on the shank portion 9 is self-tapping in cancellous bone. Also in the preferred embodiment, the thread 10 starts substantially at the distal end 4 of the body member 3. As is shown in FIG. 4, the fixation screw of the present invention is preferably formed with one or more flutes 12 in the shank portion 9 and thread 10 to improve the ability of the thread 10 to tap into cancellous bone. As is also shown in FIG. 4, the thread 10 extends from the distal end 4 of the body member 3 to better anchor the fixation screw in bone 2.

Figure 3:
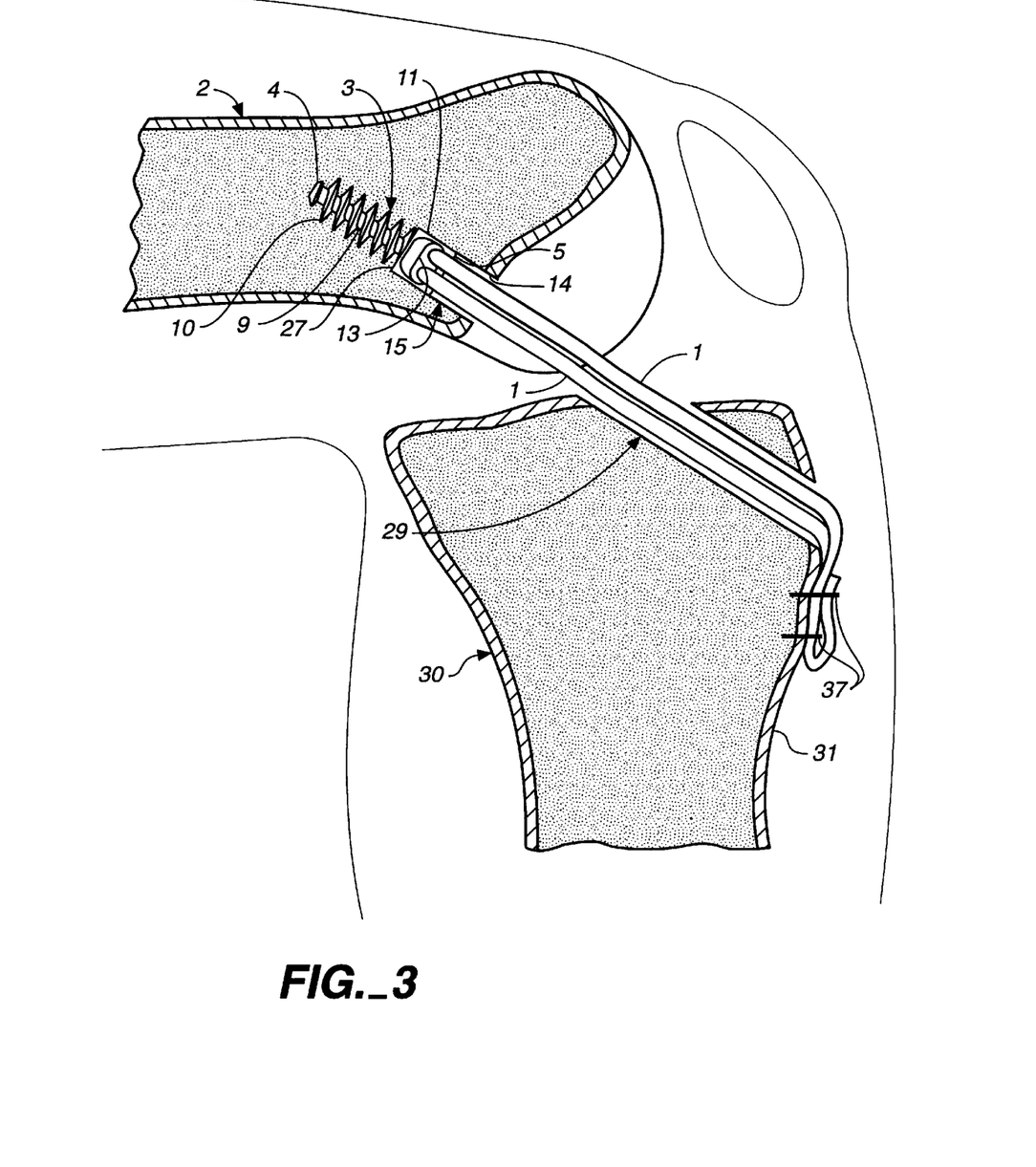
FIG. 3 is a schematic cross section of a knee in flexion. Portions of the femur and tibia are shown. The fixation screw is shown placed in the femur. Two grafts are received by the eyelet of the fixation screw. The two grafts are shown attached to the tibia cortical surface with bone staples near the entrance of the tibial tunnel.

As is shown in FIG. 3, in the preferred embodiment of the present invention the means for securing the graft 1 to the head portion 11 is an eyelet 13 formed in the head portion 11 that is large enough to receive the graft 1. The graft 1 is looped or threaded through the eyelet 13. As is shown in FIG. 3, the graft 1 preferably consists of two separate members, specifically the gracilis tendon and the semitendinosus tendon.

As is shown in FIG. 4, in the preferred embodiment of the present invention, the central axis 6 bisects the eyelet 13, such that when the graft 1 consists of only one member, it can align with the central axis 6. When two separate members are used for the graft 1, the position of the eyelet 13 in relation to the central axis 6 helps the separate members of the graft 1 to be positioned as closely as possible to the central axis 6 and away from the side wall 14 of the endosteal tunnel 15 in which the fixation screw is being inserted. FIG. 3 shows a closed-end, endosteal tunnel 15 formed in the femur 2 which for short-hand purposes is called a femoral endosteal tunnel 15.

Figure 2:
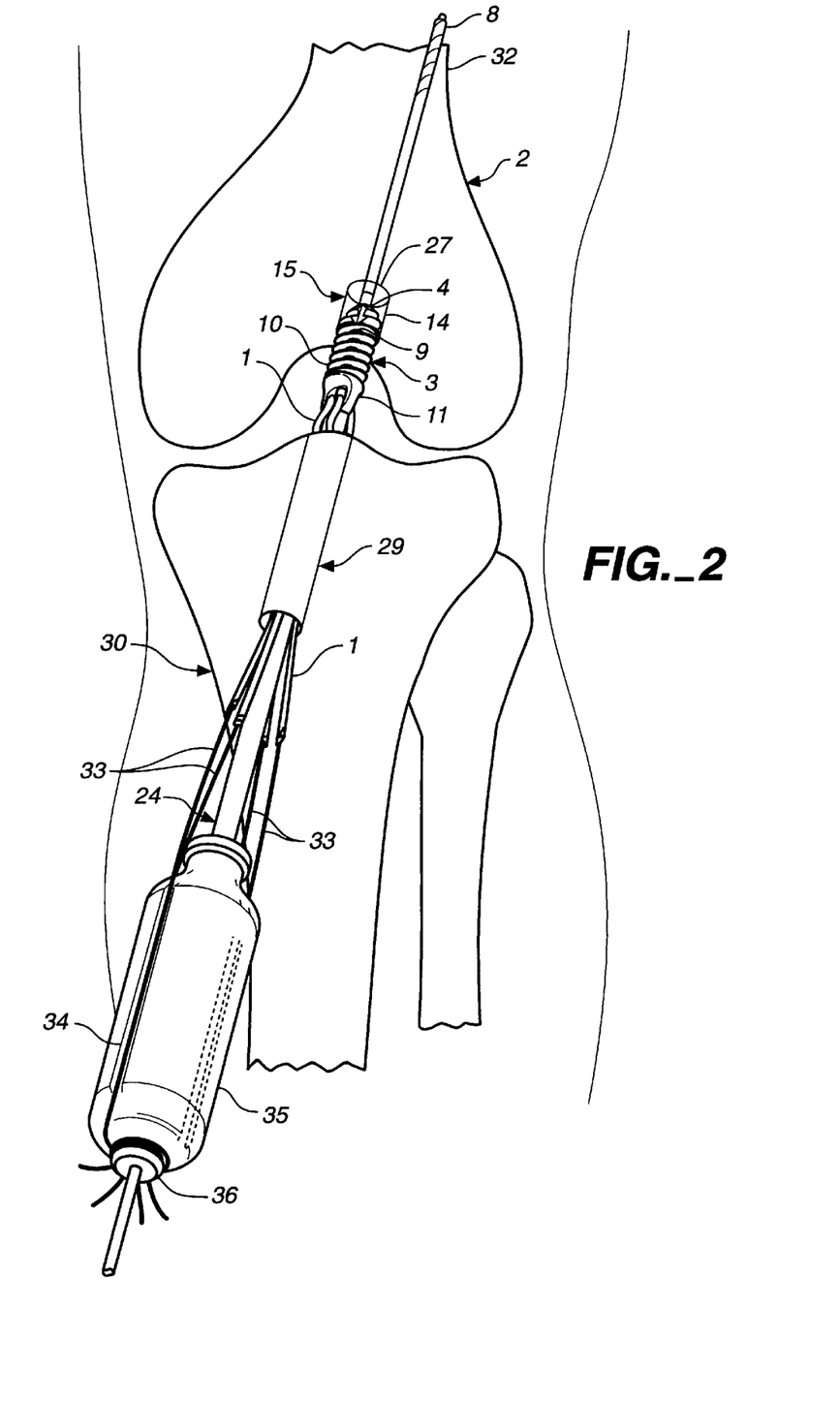
FIG. 2 is a schematic anterior view of the left knee in flexion. A driver is shown inserted over the guide drill. The fixation screw of the present invention is attached to the driver and is partially inserted into the closed end femoral tunnel. Two grafts are shown looped through the eyelet of the present invention. Sutures, attached to the ends of the grafts, pass through grooves on the driver handle and are tied at a button on the end of the driver.

As is best shown in FIGS. 2 and 4, in the preferred embodiment of the present invention, the diameter of the eyelet 13 is larger than the width of the cannula 7 such that the cannula 7 can receive a guide drill 8 for positioning the fixation screw at the same time that the graft 1 is received by the eyelet 13.

As is best shown in FIG. 3, the eyelet is shaped so that the graft is moved away from the side wall 14 of the endosteal tunnel 15 when it is pulled taut so as to prevent damage to the graft 1 due to abrasion with the side wall 14 of the endosteal tunnel 15. This is accomplished by forming the eyelet 13 so that it approaches an ellipse or oval in shape.

Figure 8:
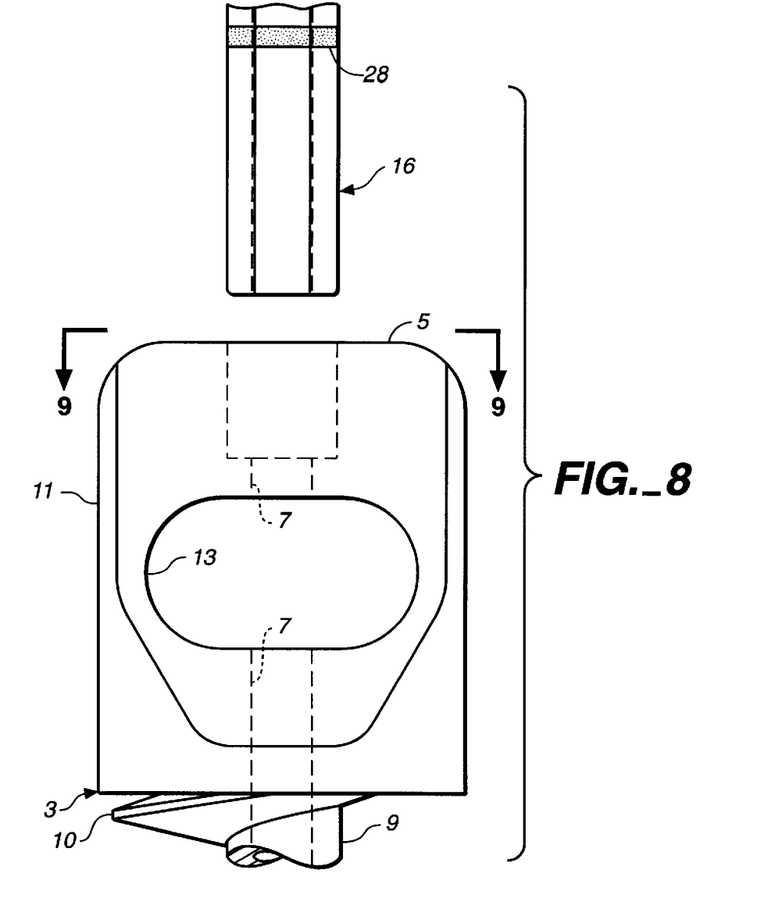
FIG. 8 is a front view of a portion of another form of the fixation screw of the present invention and a portion of a driver for inserting the fixation screw. The head portion and part of the shank portion of the fixation screw are shown. The fixation screw is shown with a portion of the cannula in the proximal end of the body member shaped to closely receive a hexagonal driver.
Figure 9:
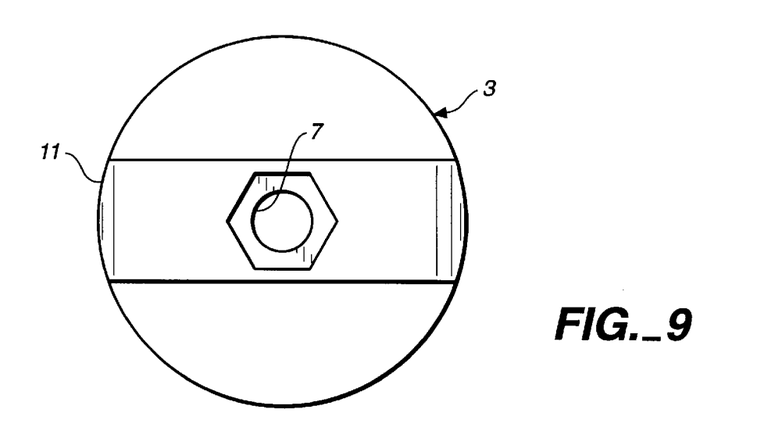
FIG. 9 is a top view of the fixation screw of the present invention, showing the head portion of the body member, taken along line 9—9 of FIG. 8.
Figure 10A:
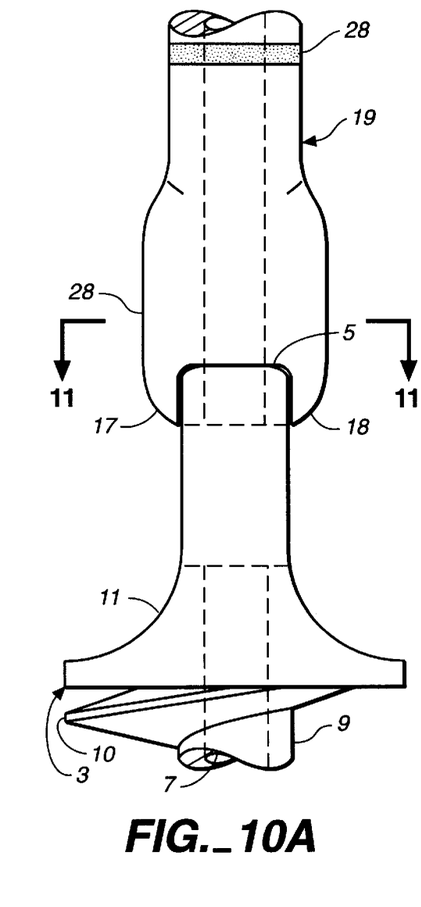
FIG. 10A is a side view of a portion of another form of the fixation screw of the present invention and a portion of a driver for inserting the fixation screw. The head portion and part of the shank portion of the fixation screw are shown. A forked driver with two prongs is shown inserted over the proximal end of the body member.
Figure 10B:
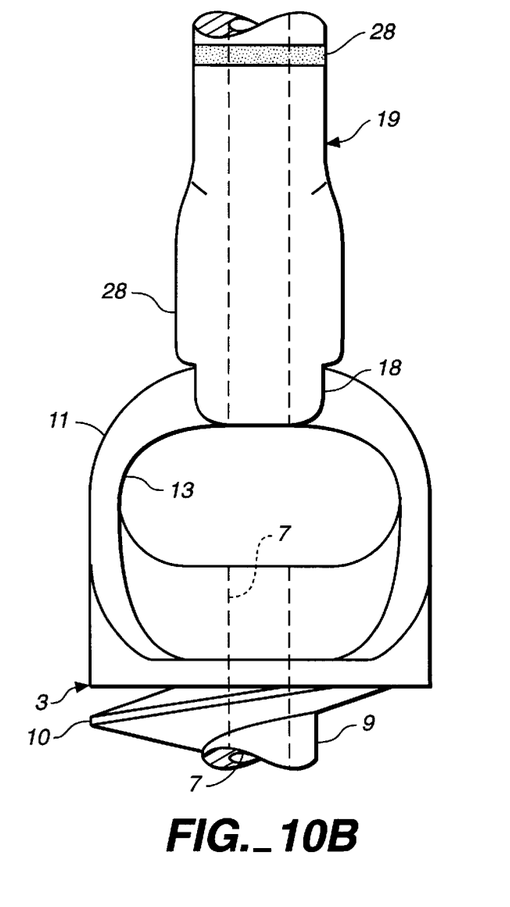
FIG. 10B is a front view of a portion of the fixation screw of the present invention and a portion of a driver for inserting the fixation screw. The head portion and part of the shank portion of the fixation screw are shown. A forked driver with two prongs is shown inserted over the proximal end of the body member.
Figure 11:
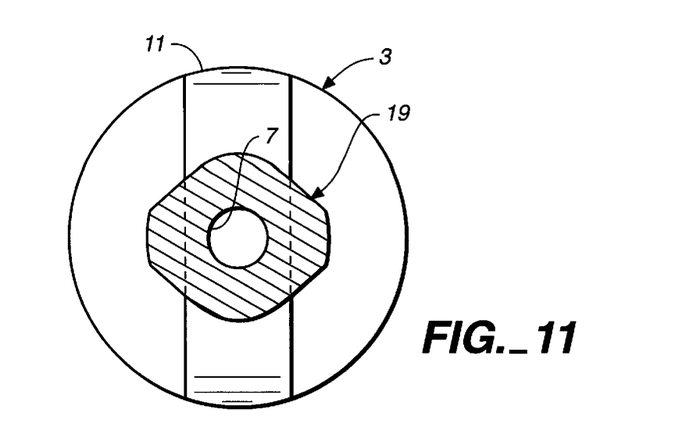
FIG. 11 is a top view of the fixation screw of the present invention, taken along line 11—11 of FIG. 10A. A portion of the forked driver is shown in cross-section.
Figure 12:
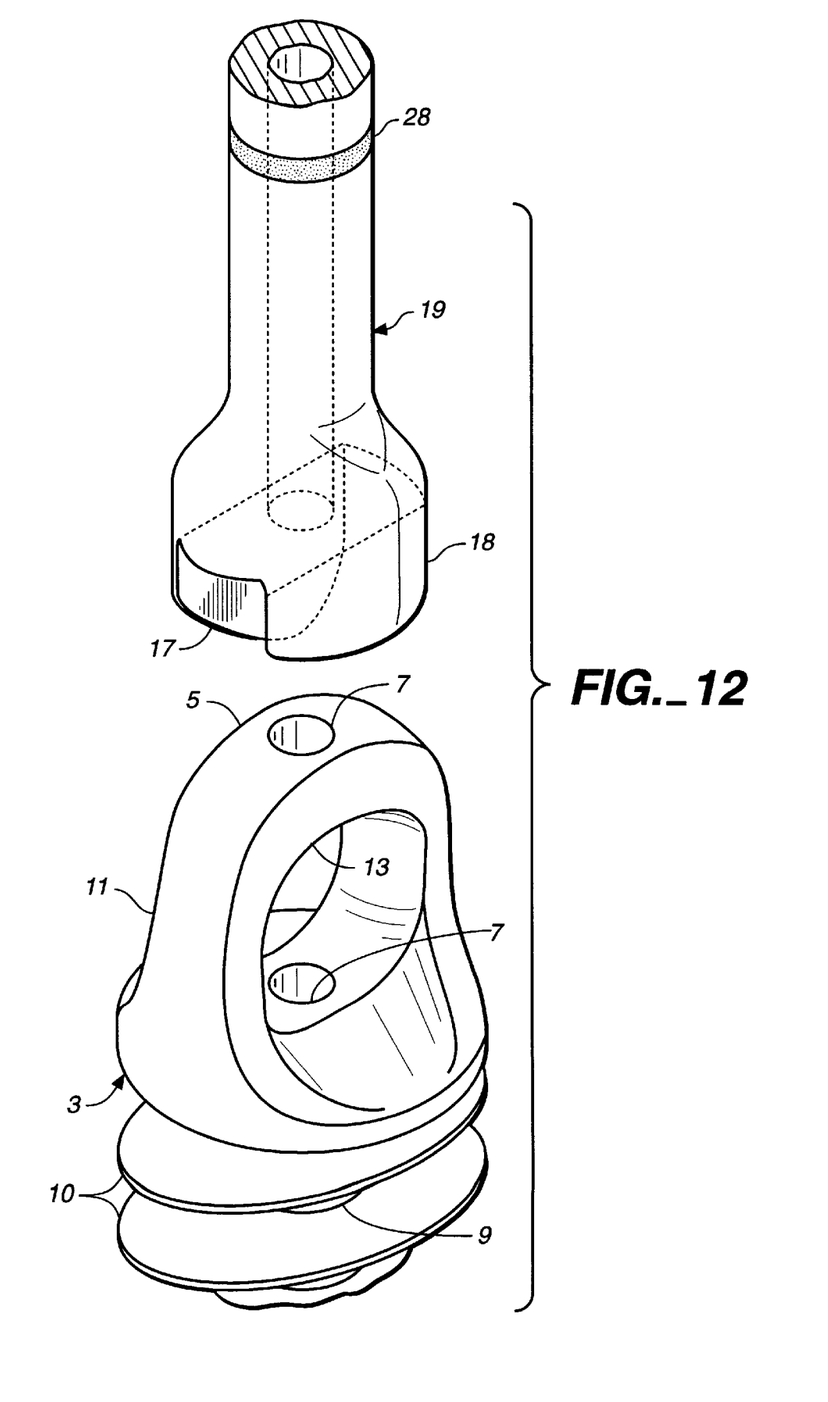
FIG. 12 is a perspective view of a portion of the fixation screw of the present invention and a portion of a driver for inserting the fixation screw. The head portion and part of the shank portion of the fixation screw are shown. A forked driver having two prongs is shown.

In one embodiment of the present invention, the means for mechanically coupling with a driver consists of forming a portion of the cannula 7 in the head portion 11 to closely receive and mechanically couple with a corresponding driver 16. As is shown in FIGS. 8 and 9, a portion of the cannula 7 in the head portion 11 is formed to closely receive and mechanically couple with a hexagonally shaped driver 16.

In another form of the present invention, the entire cannula 7 in the head portion 11 can be formed to closely receive and mechanically couple with a driver, such that the driver as well as the guide drill 8 passes through the eyelet 13. In such an embodiment, the diameter of the eyelet 13 should be larger than the width of the cannula 7, such that the cannula 7 in the head portion 11 can receive a guide drill 8 for positioning the fixation screw and a driver for inserting the fixation screw at the same time that the graft 1 is received by the eyelet 13.

As is shown in FIGS. 10A, 10B, 11 and 12, in another form of the present invention the means for mechanically coupling with the driver can consist of the proximal end 5 of the body member 3 formed to be closely received between cooperating prongs 17 and 18 of a driver 19.

As is shown in FIGS. 4, 5, 6 and 7 in the preferred form of the invention the means for mechanically coupling with the driver consists of forming two bores 20 and 21 in the head portion 11 of the body member 3 that can receive corresponding extensions 22 and 23 on a special driver 24. In the preferred form, the pair of bores 20 and 21 in the head portion 11 are cylindrical and couple with a cannulated driver 24 with corresponding cylindrical extensions 22 and 23. The preferred means for mechanically coupling with the driver allows the head portion 11 to be formed so as to provide maximum room for the graft 1 to pass around the proximal end 5.

In the preferred embodiment of the fixation screw, the minor diameter 25 of the shank 9 will be approximately 30% of the major diameter 26 of the thread 10. The minor diameter 25 is minimized to lessen the displacement of cancellous bone when only a drill guide 8 is used to prepare the bone 30 for the insertion of the threaded shank 9 past the closed end 27 of the endosteal tunnel 15.

The driver 16, 19, or 24 is preferably marked so that when the fixation screw of the present invention is fully seated in the bone 2, a mark 28 on the driver 1 6, 19, or 24 will align with the entrance of the endosteal tunnel 15.

The present invention can be formed of metal (e.g. 316 stainless steel or titanium), a non-absorbable polyethylene, an absorbable polylactic acid substance, or an absorbable polyglycolic acid substance to name a few bio-compatible substances.

Figure 1:
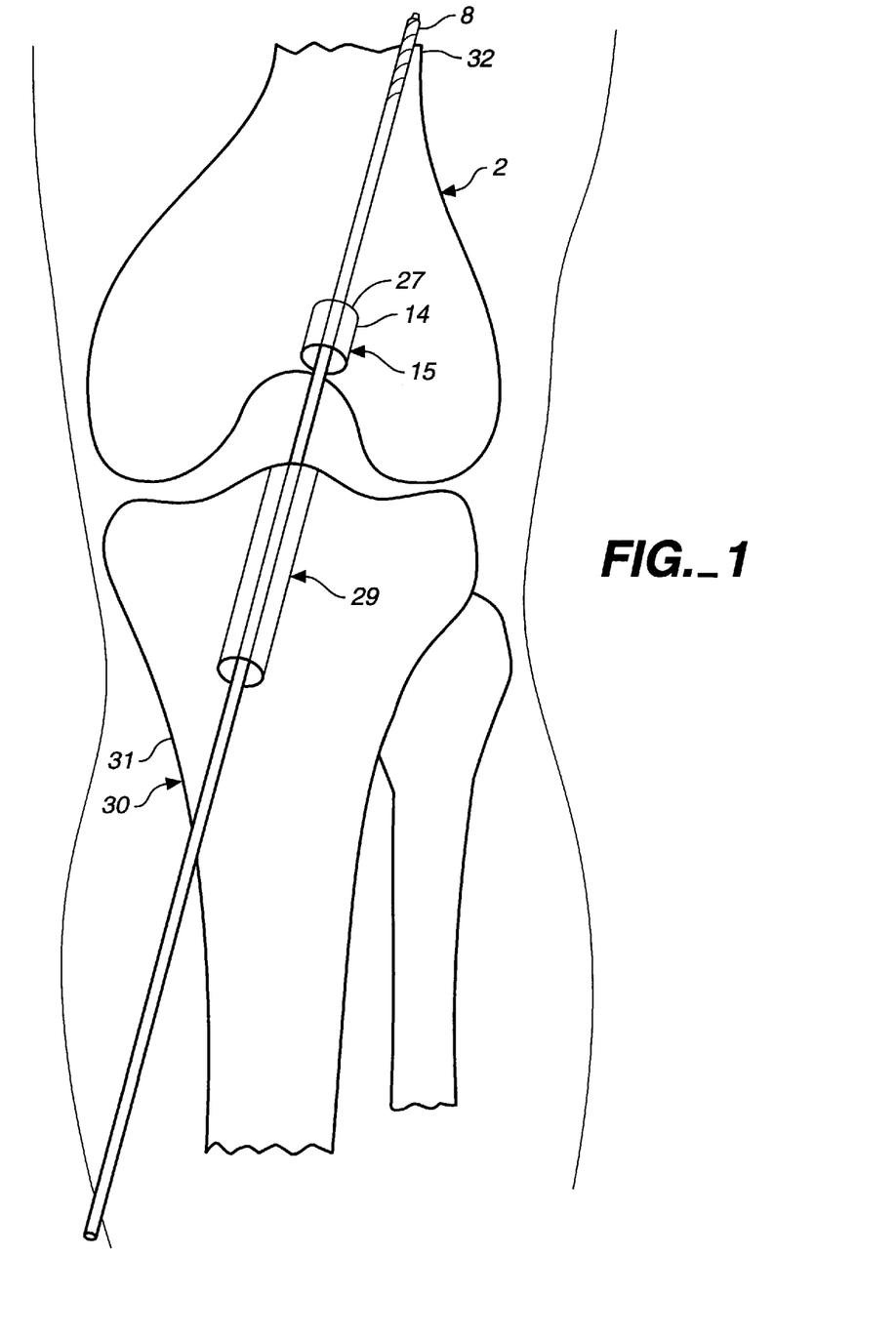
FIG. 1 is a schematic anterior view of the left knee in flexion. Portions of the femur, tibia and fibula are shown with a tibial tunnel and a closed end, femoral, endosteal tunnel having been drilled in the tibia and femur respectively. The knee is shown with a guide drill in place, passing through the tibial tunnel and the femoral endosteal tunnel for receiving the fixation screw of the present invention.

With reference to FIGS. 1, 2 and 3, preferably, the intra-articular tendon sling fixation screw of the present invention is used in arthroscopic ACL reconstruction surgery in the following manner.

A tibial tunnel 29 is formed in the tibia 30 with its entrance at the tibial cortex 31 and its exit at the attachment site of the anterior cruciate ligament on the tibia 30. A tibial guide is used to determine the insertion point for the guide drill 8. The guide drill 8 is inserted into and through the tibia 30 at the proper angle. Using the guide drill 8 as a guide, a coring drill removes a section of the tibia 30 forming the tibial tunnel 29. The bone section removed by the coring drill is used to create bone plugs which are inserted into the tibial tunnel 29 and the femoral endosteal tunnel 15 at the end of the procedure.

Next the location of the closed-end endosteal tunnel 15 in the femur 2 is determined. The endosteal tunnel 15 is to be formed in the femur 2 with its entrance at the attachment point of the anterior cruciate ligament with the femur 2. This tunnel is also known as a femoral endosteal tunnel 15. A femoral tunnel guide is used to determine the correct angle and point of entry for the endosteal tunnel 15 into the femur 2. A guide drill 8 is then drilled into the femur 2 in the correct anatomic position—the insertion point of the ACL in the femur 2—using the femoral tunnel guide as a pilot. The guide drill 8 serves to mark the anatomic position for subsequent boring. The guide drill 8 is preferably drilled into the femur 2 deep enough to engage the anterior lateral femoral cortex 32. This prevents the guide drill 8 from backing out. The guide drill 8 also passes through the tibial tunnel 29.

The femoral endosteal tunnel 1 5 is then formed using a cannulated acorn drill that fits over the guide drill 8. The femoral endosteal tunnel 15 should be drilled 1 mm larger than the major diameter 26 of the thread 10, so as to facilitate insertion of the fixation screw into the closed-end, endosteal tunnel 15. The appropriately sized acorn drill is thus 1 mm larger than major diameter 26 of the thread 10 of the fixation screw. The femoral endosteal tunnel 15 should be drilled deep enough to completely receive the head portion 11 of the fixation screw and a bone plug when the threaded shank 9 of the fixation screw has been completely inserted into the femur 2.

The acorn drill is then removed. The intra-articular tendon sling fixation screw of the present invention is then prepared. The graft 1 is looped through the eyelet 13 of the fixation screw. In the preferred embodiment, the graft 1 consists of both the semitendinosus and gracilis tendons for added strength. The fixation screw is then inserted over the drill guide 8, with the semitendinosus tendon looped through the eyelet 13 on one side of the drill guide 8 and the gracilis tendon looped through the eyelet 13 on the other sided of the drill guide 8.

Next the preferred driver 24 is inserted over the drill guide 8 and releasably attached to the fixation screw. In the preferred embodiment of the fixation screw, a pair of cylindrical bores 20 and 21, formed in the head portion 11, couple with corresponding cylindrical extensions 22 and 23 on the cannulated driver 24. Prior to threading the graft 1 into the eyelet 13 of the fixation screw, sutures 33 are attached to the ends of the grafts 1. These sutured ends of the grafts 1 are then pulled taut, with the attached sutures 33 fitting into grooves 34 on the sides of the handle 35 of the driver 24. The sutures 33 are tied off on a button 36 on the driver 24. Pulling the grafts 1 taut causes them to move away from the side wall 14 of the femoral endosteal tunnel 15 so they cannot be abraded. With the sutures 33 tied off on the button 36 and nestled in the grooves 34 of the driver handle 35, the grafts 1 will turn with the driver 24 and not twist.

The fixation screw is then inserted into the femoral endosteal tunnel 15. When the distal end 4 of the fixation screw touches the closed end 27 of the femoral endosteal tunnel 15, the surgeon begins to drive the fixation screw into the femur 2 by rotating the driver 24 and applying pressure. The surgeon can tell when the fixation screw has been driven into the bone 2 to a sufficient depth by referring to markings 28 on the driver 24 which will align with the entrance of the femoral endosteal tunnel 15 when the fixation screw is fully seated in the bone 2.

When the fixation screw is in place, the sutures 33 attached to the ends of the grafts 1 are removed from the driver 24. Then the driver 24 and the drill guide 8 are removed. The grafts 1 are pulled taut and fixed to the tibial cortex 31 near the entrance of the tibial tunnel 29 by means of staples 37 in a pants-over-vest attachment system. Then the sutures 33 are cut at the ends of the grafts 1.

The bone plugs fashioned from the tibial bone section removed by the coring drill are then placed in the femoral endosteal tunnel 15 and the tibial tunnel 29 to allow bone to tendon healing.

If a self-tapping form of the fixation screw is not used, then a step must be added. After the femoral endosteal tunnel 15 is formed with the acorn drill. A tap must be used to pre-cut a path in the cancellous bone at the closed end 27 of the femoral endosteal tunnel 15 for the threaded shank portion 9 of the fixation screw.

The invention is not limited to the specific form shown, but includes all forms within the definitions of the following claims.

I claim:

1. A ligament reconstruction graft fixation screw for securing a graft to a bone having a tunnel formed therein comprising:

a. a body member, having a distal end, a proximal end, a central axis and a cannula through said central axis of said body member;

b. a shank portion, having an external screw thread; and c. a head portion rigidly and fixedly coupled to said shank portion so that said head portion moves in unison with said shank portion, said head portion being formed with means for mechanically coupling with a driver, said head portion having an eyelet that is large enough to receive said graft, and the diameter of said eyelet is larger than the width of said cannula.

* * * * *